United States Patent
Cho et al.

(10) Patent No.: US 11,426,120 B2
(45) Date of Patent: Aug. 30, 2022

(54) METHOD AND DEVICE FOR MEASURING SLEEP EFFICIENCY BY USING RADAR

(71) Applicant: WRT LAB CO., LTD., Seoul (KR)

(72) Inventors: Sung Ho Cho, Seoul (KR); Jeong Woo Choi, Seoul (KR); Seok Hyun Cho, Seoul (KR)

(73) Assignee: WRT LAB CO., LTD., Seoul (KR)

( * ) Notice: Subject to any disclaimer, the term of this patent is extended or adjusted under 35 U.S.C. 154(b) by 553 days.

(21) Appl. No.: 16/473,768

(22) PCT Filed: Dec. 29, 2017

(86) PCT No.: PCT/KR2017/015730
§ 371 (c)(1),
(2) Date: Jun. 26, 2019

(87) PCT Pub. No.: WO2018/124812
PCT Pub. Date: Jul. 5, 2018

(65) Prior Publication Data
US 2021/0128057 A1    May 6, 2021

(30) Foreign Application Priority Data
Dec. 30, 2016  (KR) .......................... 10-2016-0183503

(51) Int. Cl.
*G08B 23/00*    (2006.01)
*A61B 5/00*    (2006.01)
(Continued)

(52) U.S. Cl.
CPC .......... *A61B 5/4815* (2013.01); *A61B 5/1118* (2013.01); *A61B 5/1121* (2013.01); *A61B 5/1126* (2013.01); *G01S 13/62* (2013.01)

(58) Field of Classification Search
CPC ... A61B 5/4815; A61B 5/1118; A61B 5/1121; A61B 5/1126; A61B 5/1116; G01S 13/62; G01S 13/88
See application file for complete search history.

(56) References Cited

U.S. PATENT DOCUMENTS 8,740,793 B2 *  6/2014  Cuddihy ................ G16H 40/67
                                                         600/301
2013/0053653 A1  2/2013  Cuddihy et al.
(Continued)

FOREIGN PATENT DOCUMENTS

JP    2012-187299 A    10/2012
JP    2013-022360 A    2/2013
(Continued)

OTHER PUBLICATIONS

K. Ota et al., "Elderly-care Motion Sensor Using UWB-IR", Sensors Applications Symposium (SAS), 2011, IEEE, Feb. 22-24, 2011.
(Continued)

*Primary Examiner* — Toan N Pham
(74) *Attorney, Agent, or Firm* — Locke Lord LLP; Scott D. Wofsy

(57) ABSTRACT

Disclosed is a method and a device for measuring sleep efficiency by using a radar, the device including: a height recognition unit recognizing a height of a measurement target person by using a signal received from the radar; a movement section extraction unit extracting a movement section of the person during sleep from the received signal, and calculating a length of the extracted movement section and an amount of movement; a normalization unit normalizing the amount of the movement by applying, to the calculated amount of the movement, a ratio between the height of the person and the length of the movement section; a sleep/wakefulness state determination unit determining
(Continued)

whether the person is in a wakefulness state or a sleep state; and a sleep efficiency calculation unit calculating the sleep efficiency.

8 Claims, 11 Drawing Sheets

(51) Int. Cl.
*A61B 5/11* (2006.01)
*G01S 13/62* (2006.01)

(56) References Cited

U.S. PATENT DOCUMENTS

2018/0106897 A1\* 4/2018 Shouldice ............ A61B 5/0507
2020/0281523 A1\* 9/2020 Maidel ................ A61B 5/4809

FOREIGN PATENT DOCUMENTS

| | | |
|---|---|---|
| JP | 2013-094340 A | 5/2013 |
| JP | 2014-512905 A | 5/2014 |
| KR | 10-2014-0003867 A | 1/2014 |
| KR | 10-2015-0114057 A | 10/2015 |

OTHER PUBLICATIONS

International Search Report issued in PCT/KR2017/015730, dated Apr. 13, 2018.

\* cited by examiner k: denotes signal sequence, namely, sample index of signal

Fig 11.

| Patients | 1 | 2 | 3 |
|---|---|---|---|
| Age | 35 | 33 | 26 |
| Gender(M/F) | M | M | M |
| Height(cm) | 175.6 | - | 171 |
| Weight(kg) | 87.9 | - | 77 |
| Sleep Efficiency from Medical Device(%) | 91.3 | 56.5 | 63.1 |
| Radar Sleep Efficiency from Radar(%) | 93.2 | 60.6 | 76.3 |
| Absolute Error Rate(%) | +1.9 | +4.1 | +13.2 |

METHOD AND DEVICE FOR MEASURING SLEEP EFFICIENCY BY USING RADAR

CROSS REFERENCE TO RELATED APPLICATIONS

This application is a U.S. National Phase Application filed under 35 U.S.C. § 371, based on Application PCT/KR2017/015730, filed Dec. 29, 2017, which application claims priority to Korean Patent Application No. 10-2016-0183503 filed on Dec. 30, 2016. The entire contents of these applications are incorporated herein by reference in their entirety.

TECHNICAL FIELD

The present invention relates generally to a method and a device for measuring sleep efficiency by using a radar. More particularly, the present invention relates to a technology for measuring sleep efficiency on the basis of a signal measured using a radar.

BACKGROUND ART

The expression "ultra-wide band (UWB)" means a radio technology in which a frequency band of 500 MHz or more is used or in which a value defined by a fractional band width that is a bandwidth of a signal compared to the center frequency is 25% or more.

That is, UWB is a radio technology using broadband frequencies and has various advantages such as high distance resolution, permeability, strong immunity against narrowband noise, and coexistence with other devices sharing a frequency.

An impulse-radio ultra-wide band (IR-UWB) radar (hereinafter, referred to as "UWB radar") technology is that such a UWB technology is grafted on radar, and is a radar technology for recognizing a surrounding environment by transmitting an impulse signal having a short duration with a broadband characteristic in the frequency domain and by receiving a signal which reflects off an object and a person.

In a UWB radar system, a signal generation unit generates an impulse signal having a time width of several nanoseconds to several picoseconds and emits the same at a wide angle or a narrow angle through a transmission antenna, and the emitted signal reflects off various objects or people and is converted into a digital signal through a reception antenna and an ADC.

Due to the advantage of this UWB radar, research has been conducted to utilize UWB radar in various fields such as a medical device for respiration and heart rate measurement, a portable radar device for lifesaving at a disaster site, a device for counting the number of people in a particular area, and so on. Recently, such fields have expanded to measuring sleep efficiency.

In general, in order to measure sleep efficiency, it is necessary to visit a specialized hospital and to have a detailed examination called polysomnography.

The polysomnography determines a sleep/wakefulness state of a person required for calculating sleep efficiency, on the basis of brainwaves and other bio signals.

In order to observe brainwave sand other bio signals, it is necessary to attach various kinds of sensors, which is inconvenient. Also, generally, the measurement is performed only one time rather than daily, and it is difficult to measure sleep efficiency every day because the price for polysomnography is very high.

Further, a sensor wearable on the wrist in the form of a band provides sleep efficiency measurement. However, this measures sleep efficiency mainly on the basis of respiration and heart rate only, so there may be a difference from the actual sleep efficiency and it is inconvenient to necessarily wear the sensor on a part of the body (the wrist, etc.).

Furthermore, in the conventional methods of measuring sleep efficiency on the basis of movement, according to the body size of a measurement target person, when the height is tall, even a small movement is determined into a big movement value, and when the height is short, even a big movement is determined into a small movement value. Therefore, there is a performance deviation according to the user's body size.

DISCLOSURE

Technical Problem

Accordingly, the present invention has been made keeping in mind the above problems occurring in the related art, and the present invention is intended to propose a method where sleep efficiency of a measurement target person is measured using a radar without wearing a separate device for sleep efficiency measurement and the accuracy of the result of the measurement is enhanced by applying the body size of the measurement target person as well as the size of the momentary movement of the measurement target person and the duration of the movement.

Technical Solution

In order to accomplish the above object, according to an embodiment of the present invention, the present invention provides a device for measuring sleep efficiency by using a radar, the device including: a height recognition unit recognizing a height of a measurement target person by using a signal received from the radar; a movement section extraction unit extracting a movement section of the measurement target person during sleep from the received signal, and calculating a length of the extracted movement section and an amount of movement; a normalization unit normalizing the amount of the movement by applying, to the calculated amount of the movement, a ratio between the height of the measurement target person and the length of the movement section; a sleep/wakefulness state determination unit determining whether the measurement target person is in a wakefulness state or a sleep state by calculating a total amount of the movement per unit length for a predetermined time on the basis of the normalized amount of the movement and by comparing the calculated total amount of the movement with a predetermined threshold value; and a sleep efficiency calculation unit calculating the sleep efficiency by using a total sleep time, a time determined into the wakefulness state during the total sleep time, the number of times that the wakefulness state is determined, and a predetermined wakefulness state maintenance time in which the wakefulness state is expected to be maintained.

In order to accomplish the above object, according to an embodiment of the present invention, the present invention provides a method of measuring sleep efficiency by a sleep efficiency measurement device using a radar, the method including: (a) recognizing a height of a measurement target person by using a signal received from the radar (b) extracting a movement section of the measurement target person during sleep from the received signal, and calculating a length of the extracted movement section and an amount of movement; (c) normalizing the amount of the movement by applying, to the calculated amount of the movement, a ratio between the height of the measurement target person and the length of the movement section; (d) determining whether the measurement target person is in a wakefulness state or a sleep state by calculating a total amount of the movement per unit length for a predetermined time on the basis of the normalized amount of the movement and by comparing the calculated total amount of the movement with a predetermined threshold value; and (e) calculating the sleep efficiency by using a total sleep time, a time determined into the wakefulness state during the total sleep time, the number of times that the wakefulness state is determined, and a predetermined wakefulness state maintenance time in which the wakefulness state is expected to be maintained.

Advantageous Effects

According to the embodiments of the present invention, sleep efficiency of the measurement target person is measured with high accuracy using a radar without wearing a separate device for sleep efficiency measurement.

Also, the accuracy of the result of the measurement is enhanced by applying the body size of the measurement target person as well as the size of the momentary movement of the measurement target person and the duration of the movement.

It should be understood that the effects of the present invention are not particularly limited to those described above, and the present invention includes all effects that can be deduced from the detailed description of the invention or the configurations of the invention described in the appended claims.

DESCRIPTION OF DRAWINGS

FIG. 11 is a result of comparison between an actual polysomnography and a sleep efficiency measurement method according to an embodiment of the present invention.

MODE FOR INVENTION

Figure 1:
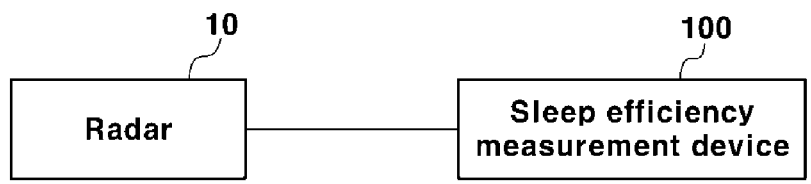
FIG. 1 is a diagram illustrating a configuration of a sleep efficiency measurement system using a radar according to an embodiment of the present invention.

A variety of modifications may be made to the present invention and there are various embodiments of the present invention, examples of which will now be provided with reference to drawings and described in detail. However, the present invention is not limited thereto, and the exemplary embodiments can be construed as including all modifications, equivalents, or substitutes in a technical concept and a technical scope of the present invention. The similar reference numerals refer to the similar elements described in the drawings.

Hereinafter, embodiments of the present invention will be described in detail with reference to the accompanying drawings.

FIG. 1 is a diagram illustrating a configuration of a sleep efficiency measurement system using a radar according to an embodiment of the present invention.

A biometric information measurement system using a radar according to an embodiment of the present invention may include a radar 10 and asleep efficiency measurement device100.

In the present invention, regarding the radar 10, an impulse-radio ultra-wide band (IR-UWB) radar may be used as an example. It is noted that the radar of the present invention is not limited to the IR-UWB radar and various radars may be used according to embodiments.

The radar 10 using one IR-UWB radar is installed at a position, for example, the ceiling, and the like, where a movement of a sleep efficiency measurement target person (hereinafter, referred to as a "measurement target person") during sleep is able to be measured, senses the movement of the measurement target person during sleep, and provides the sensed signal to the sleep efficiency measurement device100.

The sleep efficiency measurement device100 receives a signal caused by the movement of the measurement target person during sleep from the radar 10 and recognizes the height of the measurement target person using the received signal.

Here, a method of recognizing the height of the measurement target person is that signal change sections before and after the measurement target person lies on a sleeping place (for example, a bed, and the like) for measuring the sleep efficiency are extracted to recognize the height of the measurement target person, or that movement sections recognized during sleep are added up and the start and end points of the sum of the movement sections are recognized for the height of the measurement target person.

Also, the height of the measurement target person which is previously input before the sleep efficiency examination is converted considering the actual installation position of the radar 10, and the converted value is recognized as the height of the measurement target person.

A method of recognizing the height of the measurement target person will be described later with reference to FIGS. 3 to 5.

Further, the sleep efficiency measurement device100 extracts the movement section during sleep of the measurement target person using the signal received from the radar 10 and calculates the length of the extracted movement section and the amount of the movement.

Here, the length of the movement section and the amount of the movement mean the length and the amount of momentary movement calculated for a signal of a particular sequence received from the radar 10.

Further, the sleep efficiency measurement device100 applies, to the amount of the movement, the ratio between the height of the measurement target person and the length of the movement and considers the absolute movement as well as the relative length of the movement compared to the height during sleep of the measurement target person, thereby reducing the performance deviation according to difference in physical conditions, such as the difference between adults and children.

For reference, the important point in measuring the sleep efficiency is separation between a wakefulness state and a sleep state. The wakefulness state medically defined is highly related to brainwaves. However, generally, when transition from the sleep state to the wakefulness state occurs, a movement of a predetermined size or more during a predetermined time is often accompanied.

Thus, the sleep efficiency measurement device100 separates the wakefulness state and the sleep state of the measurement target person by applying the momentary movement and the duration of the movement during sleep of the measurement target person, and on the basis of this, measures the sleep efficiency.

Hereinafter, a configuration of the sleep efficiency measurement device100 will be described in detail with reference to FIG. 2.

Figure 2:
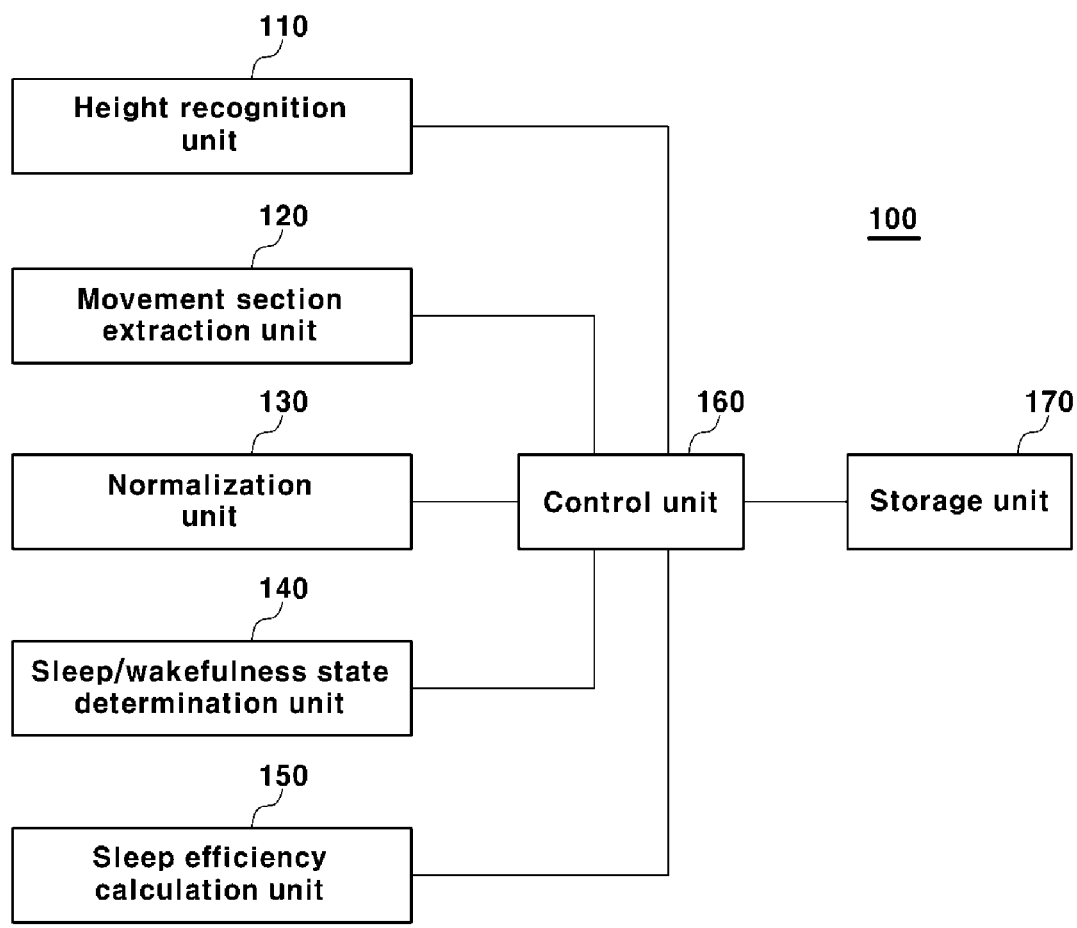
FIG. 2 is a block diagram illustrating a configuration of asleep efficiency measurement device according to an embodiment of the present invention.

FIG. 2 is a block diagram illustrating a configuration of a sleep efficiency measurement device according to an embodiment of the present invention.

Hereinafter, while describing the elements shown in FIG. 2, the description will be made with reference to FIGS. 3 to 9.

Figure 3:
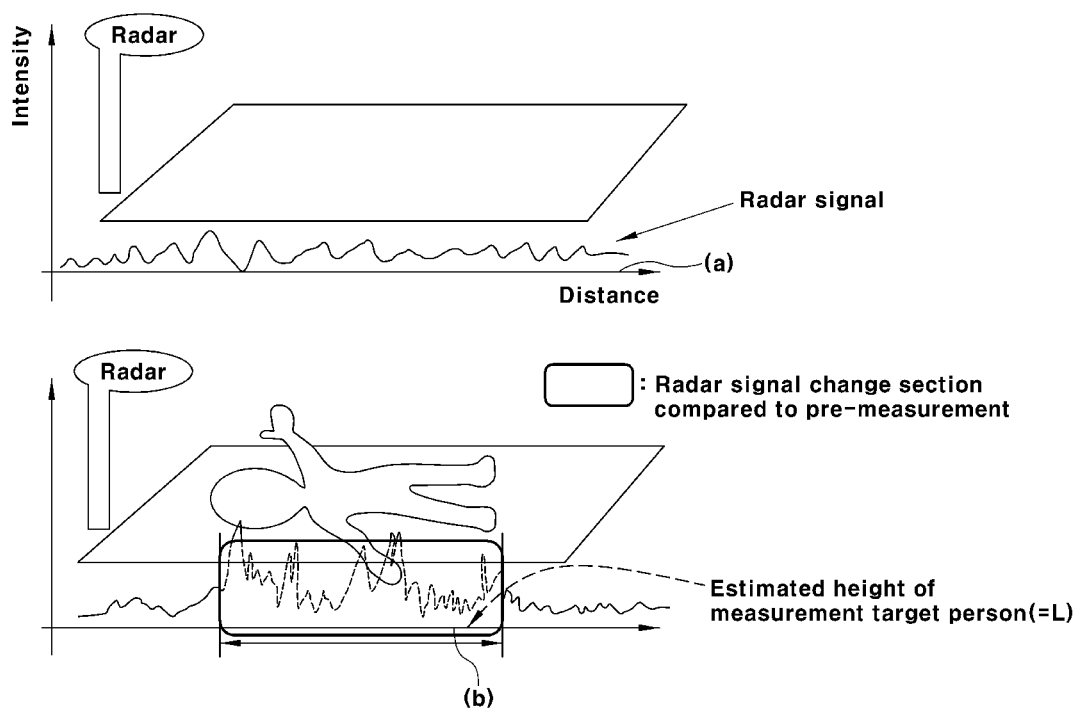
FIGS. 3 to 5 are diagrams illustrating a method of recognizing a height of a measurement target person.
Figure 4:
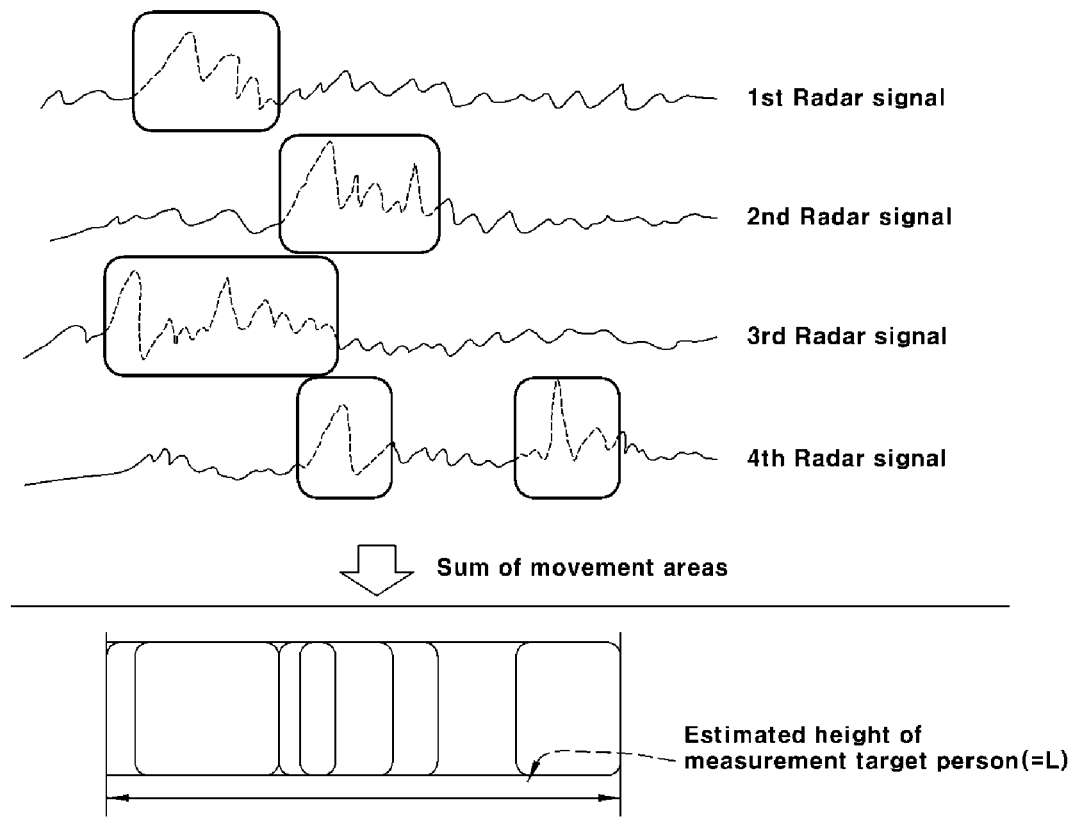
Figure 5:
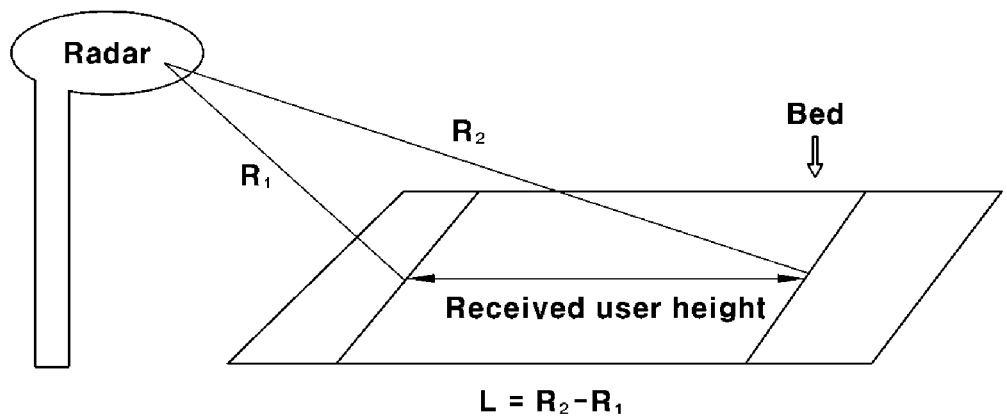
Figure 6:
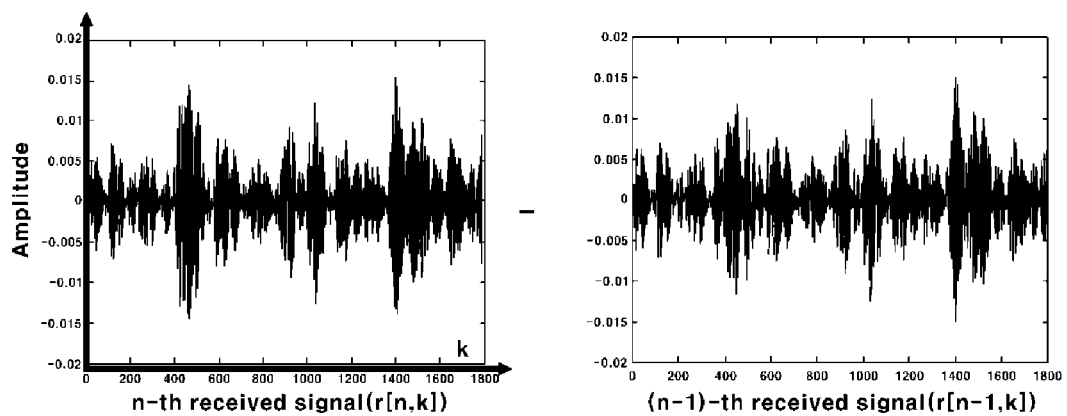
FIG. 6 is a diagram illustrating a method of calculating a difference between two signals consecutively received according to an embodiment of the present invention.
Figure 6:
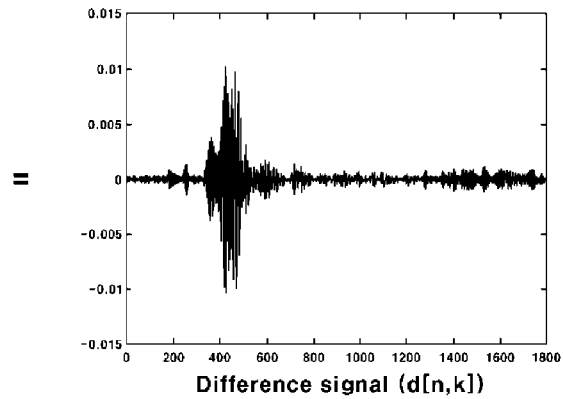
Figure 7:
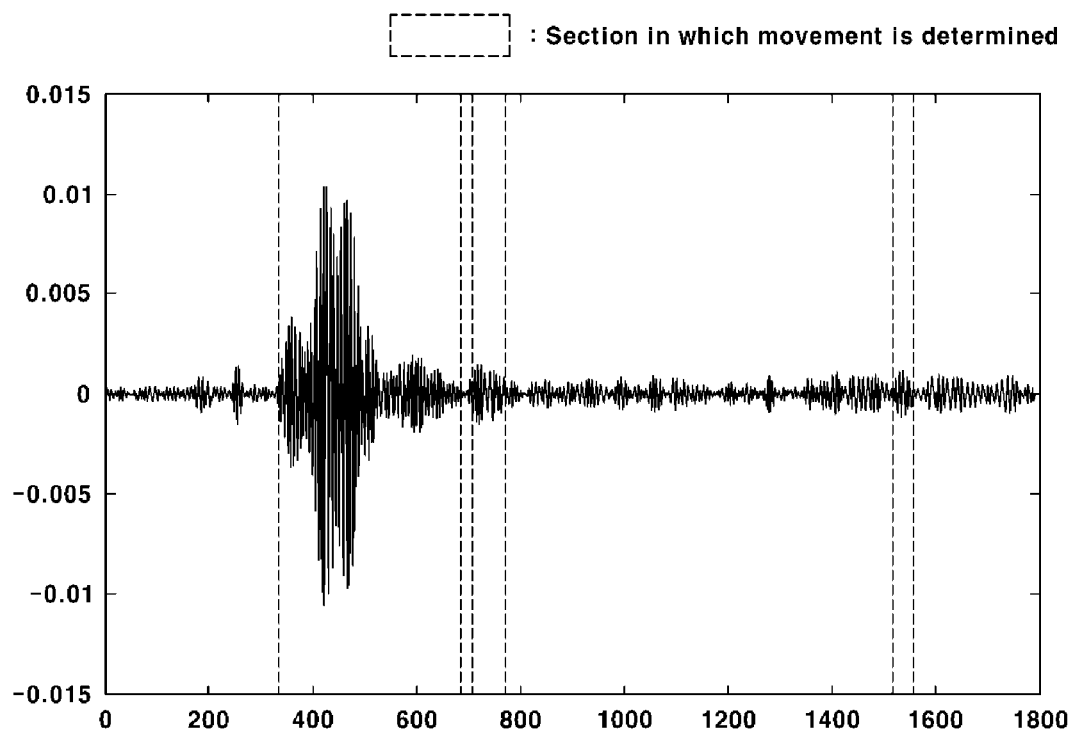
FIG. 7 is a diagram illustrating extraction of a movement section during measurement target's sleep according to an embodiment of the present invention.

FIGS. 3 to 5 are diagrams illustrating a method of recognizing a height of a measurement target person. FIG. 6 is a diagram illustrating a method of calculating a difference between two signals consecutively received according to an embodiment of the present invention. FIG. 7 is a diagram illustrating extraction of a movement section during measurement target's sleep according to an embodiment of the present invention.

Figure 8:
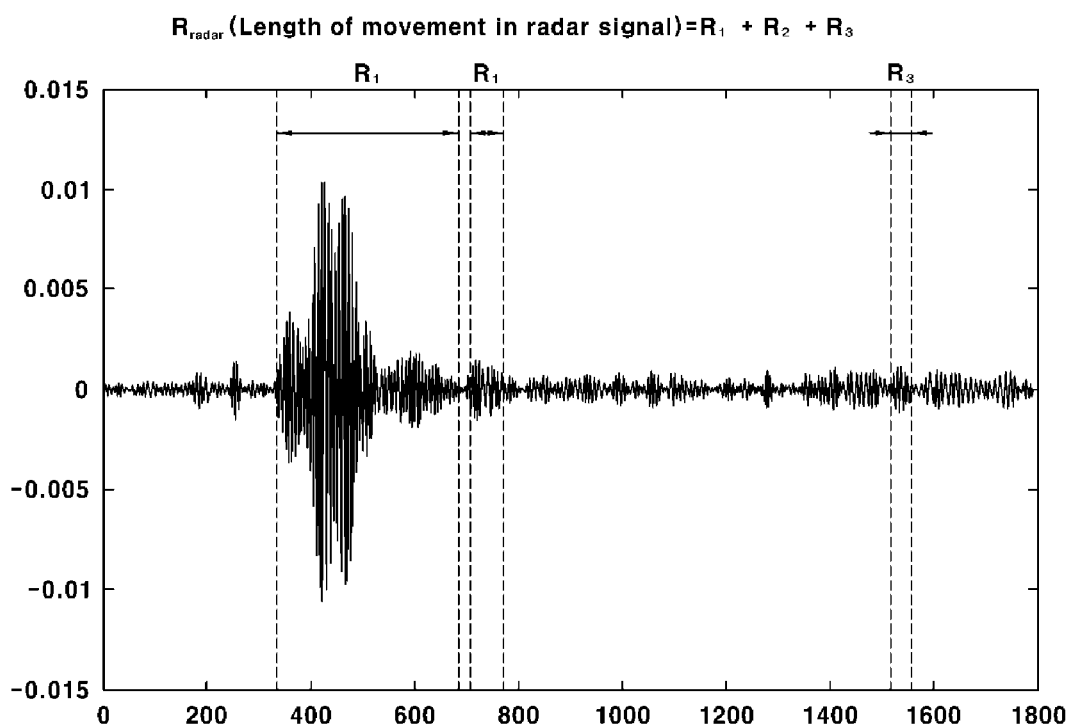
FIG. 8 is a diagram illustrating a method of measuring a length of a movement section in a radar signal according to an embodiment of the present invention.
Figure 9:
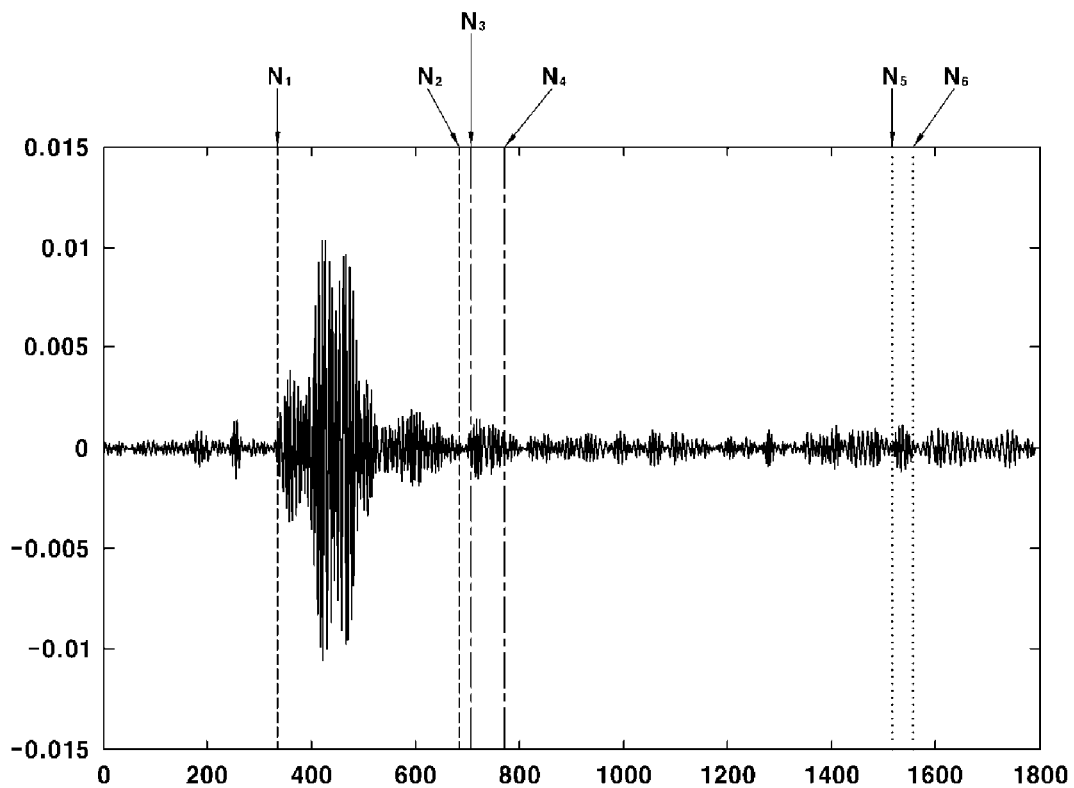
FIG. 9 is a diagram illustrating a method of calculating the amount of momentary movement when receiving the n-th signal according to an embodiment of the present invention.

Further, FIG. 8 is a diagram illustrating a method of measuring a length of a movement section in a radar signal according to an embodiment of the present invention. FIG. 9 is a diagram illustrating a method of calculating the amount of momentary movement when receiving the n-th signal according to an embodiment of the present invention.

According to the embodiment of the present invention, the sleep efficiency measurement device100 includes a height recognition unit110, a movement section extraction unit120, a normalization unit130, asleep/wakefulness state determination unit140, asleep efficiency calculation unit150, a control unit160, and a storage unit170.

Describing each element, the height recognition unit110 recognizes the height of the measurement target person.

To this end, the height recognition unit110 extracts a radar signal for the sleeping place (for example, a bed, and the like) before the sleep efficiency measurement and the signal change section after the measurement target person lies on the sleeping place, thereby recognizing the height of the measurement target person.

Referring to FIG. 3 as an embodiment for recognizing the height of the measurement target person, the radar signal before the measurement target person lies on the sleeping place is shown in (a).

There is no moving object, so the intensity with the distance is constant without big change.

However, when the measurement target person lies on the sleeping place, the signal change section occurs due to the measurement target person. The height recognition unit110 estimates the height of the measurement target person on the basis of the radar signal change section in post-measurement (b) compared with pre-measurement (a).

Further, as another embodiment for recognizing the height of the measurement target person, a change occurrence section in a radar signal caused by movement during sleep of the measurement target person is used.

Regarding this, referring to FIG. 4, a change occurrence section in a radar signal caused by movement of the measurement target person is shown.

Here, the first radar signal to the fourth radar signal may be consecutive in time or may not be consecutive.

The height recognition unit110 estimates the height of the measurement target person by using (adding the change occurrence sections) the change occurrence section in the radar signal caused by movement of the measurement target personas shown in FIG. 4.

That is, in the result of adding up the change occurrence sections, the distance from the start point to the end point is recognized for the height of the measurement target person.

Further, as still another embodiment for recognizing the height of the measurement target person, referring to FIG. 5, the height of the measurement target person is input by the user (medical staff, and the like) and is recognized by being converted into a distance considering the actual installation position of the radar.

In the meantime, the movement section extraction unit120 measures every moment of the movement of the measurement target person during sleep.

To this end, the movement section extraction unit120 uses a difference between consecutively received signals, which is represented by the following Equation.

$$M_{pre}[n] = \sum_{k=1}^{N} |r[k, n] - r[k, n-1]|$$ [Equation 1]

Here, k denotes a variable indicating a signal sequence after sampling; n denotes a number of a received signal, namely an iteration number; and N denotes the total length of the signal.

Further, r[k, n] denotes a received signal; and M pre[n] denotes a movement value calculated using the difference between consecutively received signals.

Assuming that the time intervals between received signals of the radar 10 are constant, a signal variation during unit time and the movement during sleep of the measurement target are proportional to each other. That is, when the movement during sleep is big, the signal variation during unit time calculated by [Equation 1] is also big.

The method of calculating a difference between two signals consecutively received is shown in FIG. 6.

As shown in FIG. 6, the movement section extraction unit120 calculates a difference signal (d[n, k]) obtained by subtracting the (n−1)-th received signal from then-th received signal.

Further, the movement section extraction unit120 extracts the movement section during sleep of the measurement target by using a simple threshold value or a detection algorithm such as constant false alarm rate (CFAR) for the movement of the measurement target during sleep obtained by [Equation 1].

The detail of this is shown in FIG. 7.

The movement section extraction unit120 determines, only when the movement (difference signal) of the measurement target during sleep exceeds a pre-determined threshold value, the movement as a meaningful movement.

For reference, CFAR is an algorithm that extracts a desired signal while reducing influence of noise, clutter, and the like contained in the received signal and adjusts the threshold value according to ambient noise and clutter level.

Further, the movement section extraction unit120 measures the length of the movement section in the radar signal on the basis of the movement section in the extracted radar signal, which is represented by the following Equation.

$$R_{radar} = R_1 + R_2 + R_3 \quad \text{[Equation2]}$$

The detail of this is shown in FIG. 8.

Further, the movement section extraction unit120 calculates the absolute values of the movement sections and adds up the resulting values to obtain the amount of the momentary movement.

The amount of the momentary movement of the measurement target person calculated when receiving the n-th signal is represented by the following Equation, which will be described with reference to FIG. 9 below.

$$M_{ins}[n] = \Sigma_{n=N_1}^{N_2} |d[n,k]| + \Sigma_{n=N_3}^{N_4} |d[n,k]| + \Sigma_{n=N_5}^{N_6} |d[n,k]| \quad \text{[Equation3]}$$

Here, Mins[n] denotes the amount of the momentary movement calculated when receiving the n-th signal. The absolute values of respective movement sections ($N_1$ to $N_2$, $N_3$ to $N_4$, and $N_5$ to $N_6$) are calculated and the resulting values are added up, whereby the amount of the movement is calculated.

In the meantime, the normalization unit130 normalizes the amount of the movement of the measurement target person by using the amount of the movement calculated by the movement section extraction unit120, the length of the movement, and the height (L) of the measurement target person.

This is represented by the following Equation.

$$M[n] = M_{ins}[n] \times \frac{R_{radar}}{L} \quad \text{[Equation4]}$$

Here, M[n] denotes the normalized amount of the movement considering the height of the measurement target person.

The meaning of [Equation 4] is that the same size of the movement is converted into a larger value when it is observed in a wide area compared to the height of the measurement target person; and the absolute size of the measured movement and the relative length of the movement compared to the height are applied as considerations.

Through this, the sleep efficiency measurement device100 of the present invention can reduce the performance deviation according to difference in physical conditions, such as the difference between adults and children.

In the meantime, the sleep/wakefulness state determination unit140 calculates the total amount of the movement of the measurement target person during a predetermined time and determine whether the measurement target person is in the wakefulness state or the sleep state by using the total amount of the movement.

First, the total amount of the movement of the measurement target person during the predetermined time is represented by the following Equation.

$$M_{Final}[n] = \frac{\sum_{i=0}^{K-1}(M[n-i])}{K} \quad \text{[Equation5]}$$

Here, K denotes the window size; and M[n] denotes the normalized amount of the movement considering the height of the measurement target person.

Afterward, the sleep/wakefulness state determination unit140 determines whether the measurement target person is in the wakefulness state or the sleep state by using the total amount of the movement, which is represented by the following Equation.

$$M_{Final}[n] \geq \text{Threshold: wakefulness state}$$

$$M_{Final}[n] < \text{Threshold: sleep state} \quad \text{[Equation6]}$$

In the meantime, the sleep efficiency calculation unit150 calculates the sleep efficiency considering that in the wakefulness state caused by the movement during sleep, the wakefulness state is maintained for a predetermined time ($\tau$) in addition to the movement time.

That is, it is possible to apply a wakefulness state maintenance time ($\tau$) in which the wakefulness state is expected to be maintained, and the wakefulness state maintenance time is pre-determined variously according to the embodiment.

This is represented by the following Equation.

$$E = \frac{T_{total} - (T_M + \tau \cdot K)}{T_{total}} \times 100 \quad \text{[Equation7]}$$

Here, E denotes the sleep efficiency; T total denotes the total time taken to try to get sleep (time spent in bed); TM denotes the time determined into the wakefulness state due to the movement; and K denotes the number of times that the state is determined as the wakefulness state due to the movement.

In the meantime, the control unit160 controls the elements of the sleep efficiency measurement device100, for example, the height recognition unit110, the movement section extraction unit120, the normalization unit130, the sleep/wakefulness state determination unit140, and the sleep efficiency calculation unit150 in such a manner as to perform the respective operations described above, and also controls the storage unit170 described later.

In the meantime, the storage unit170 stores an algorithm for the control unit160 to control the elements of the sleep efficiency measurement device100, data for the algorithm, and various types of data derived from the control process.

Figure 10:
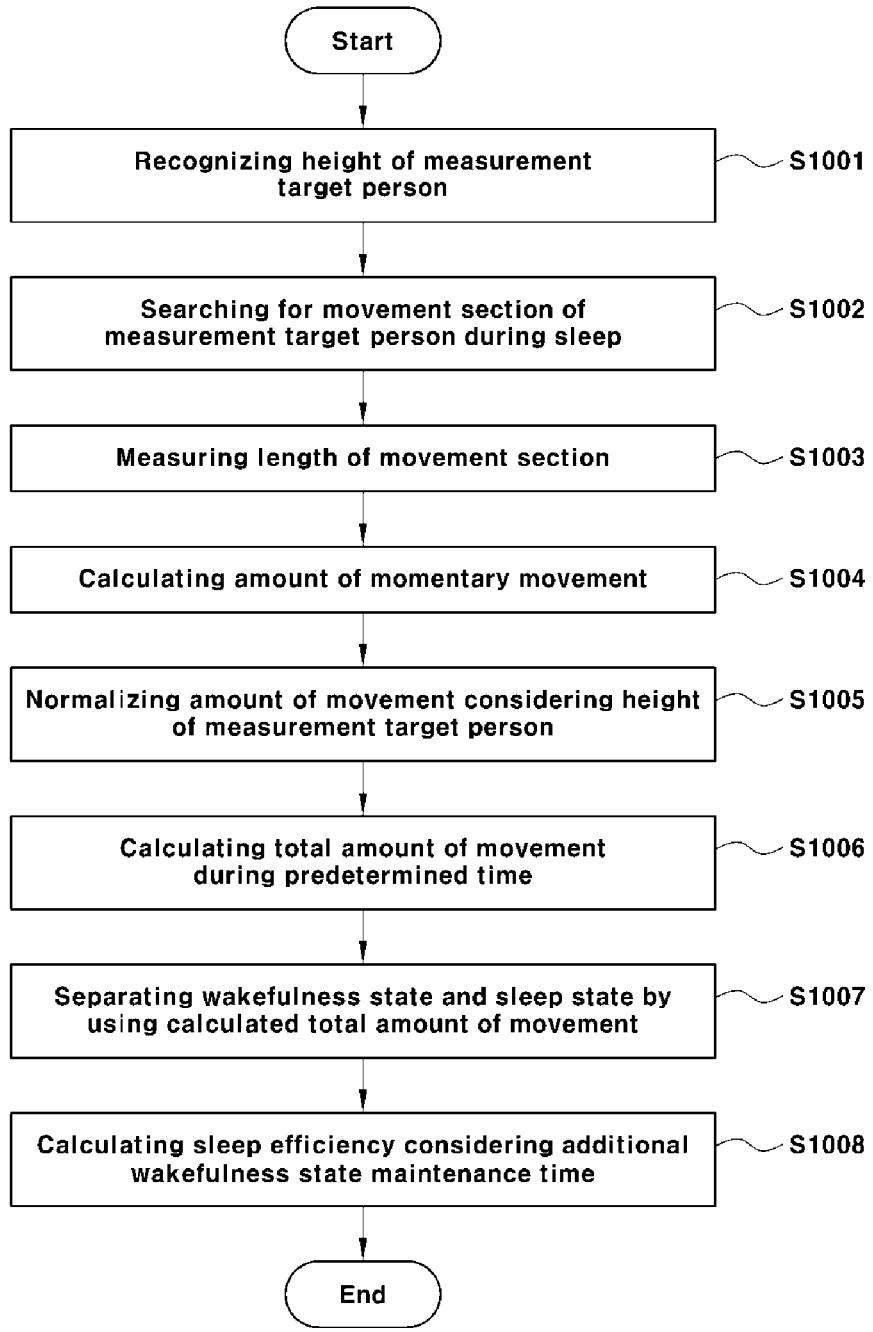
FIG. 10 is a flowchart illustrating a process of measuring sleep efficiency by using a radar according to an embodiment of the present invention.

FIG. 10 is a flowchart illustrating a process of measuring sleep efficiency by using a radar according to an embodiment of the present invention.

The flowchart of FIG. 10 may be performed by the sleep efficiency measurement device100 shown in FIG. 2.

First, the sleep efficiency measurement device100 recognizes the height (stature) of the measurement target person at step S1001.

Here, as the methods of recognizing the height of the measurement target person as shown in FIGS. 3 to 5, the height is recognized using the change sections in the radar signal before and after the measurement target person lies on the sleeping place or adding up the areas of the movement recognized during sleep. Alternatively, the height of the measurement target person input by the user (medical staff, and the like) is converted considering the actual installation position of the radar.

After step S1001, the sleep efficiency measurement device100 extracts the movement section of the measurement target person during sleep from the radar signal at step S1002.

Here, the "movement section" is calculated using the difference between two signals consecutively received, wherein [Equation 1] is used.

For reference, in extracting the movement section, only when the movement exceeds the pre-determined threshold value, is determined as the meaningful movement.

After step S1002, the sleep efficiency measurement device 100 measures the length of the movement section in the radar signal on the basis of the extracted movement section at step S1003.

Here, [Equation 2] is used for the length of the movement section.

After step S1003, the sleep efficiency measurement device 100 calculates the amount of the momentary movement when receiving a signal of a particular sequence at step S1004.

Here, the sleep efficiency measurement device 100 calculates the amount of the momentary movement by using the absolute values in respective movement sections which occur when receiving the signal of the particular sequence and by using the sum of the absolute values, wherein [Equation 3] is used.

After step S1004, the sleep efficiency measurement device 100 normalizes the amount of the movement considering the height of the measurement target person, on the basis of the length of the movement section, the height of the measurement target person, and the amount of the momentary movement at step S1005.

This is to reduce the performance deviation according to difference in physical conditions, such as the difference adults and children, by taking into consideration the absolute size of the movement as well as the relative length of the movement compared to the height, wherein [Equation 4] is used.

After step S1005, the sleep efficiency measurement device 100 calculates the total movement for a predetermined time at step S1006.

For the total amount of the movement of the measurement target person during the predetermined time, [Equation 5] is used.

After step S1006, the sleep efficiency measurement device 100 separates the wakefulness state and the sleep state by comparing the predetermined threshold value with the total amount of the movement of the measurement target person for the predetermined time at step S1007.

For separation between the wakefulness state and the sleep state, [Equation 6] is used.

After step S1007, the sleep efficiency measurement device 100 calculates the sleep efficiency considering that the wakefulness state is maintained for a predetermined time in addition to the movement time at step S1008.

Here, the sleep efficiency is calculated on the basis of the total time taken to try to get sleep (time spent in bed), the time determined into the wakefulness state due to the movement, and the number of times that the state is determined as the wakefulness state due to the movement, wherein Equation 7 is used.

FIG. 11 is a result of comparison between an actual polysomnography and a sleep efficiency measurement method according to an embodiment of the present invention.

The IR-UWB radar was installed in the polysomnography room, and radar data was measured for three patients who were subjected to polysomnography, and was compared to medical data.

FIG. 12 shows the result of the sleep efficiency, wherein the sleep efficiency was calculated using [Equation 7] for the three patients.

Referring to FIG. 12, the sleep efficiencies were 93.2%, 60.6%, and 76.3%. Absolute errors of 1.9%, 4.1%, and 13.2% were obtained with respect to the medial data from the actual polysomnography and there was no significant difference.

Here, all the error ratios for the three patients were positive values "+" because it was estimated that the state was determined as the wakefulness state due to brainwaves although the movement was not accompanied.

However, the error ratio for the third patient was relatively large because it was analyzed that the patient stopped moving and remained in the wakefulness state for a long time during sleep.

Further, when comparing the sleep efficiencies between the patients, it was found that the order of sleep efficiency measured with the medical data matches the order of sleep efficiency measured by radar.

A threshold value used for determination was set to seven equally for all the three patients, which represents the degree in which the body moves for about two seconds.

The technical details described above may be embodied as program commands executable by various computer means and may be recorded on a computer-readable recording medium.

The computer-readable recording medium may include program commands, data files, data structures, and the like separately or in combinations.

The program commands to be recorded on the computer-readable recording medium may be specially designed and configured for embodiments of the present invention or may be well-known to and be usable by those skilled in the art of computer software.

Examples of the computer-readable recording medium include magnetic recording media such as hard disks, floppy disks and magnetic tapes; optical data storage media such as CD-ROMs or DVD-ROMs; magneto-optical media such as floptical disks; and hardware devices, such as read-only memory (ROM), random-access memory (RAM), and flash memory, which are particularly structured to store and implement the program instruction.

Examples of the program instructions include not only a mechanical language code formatted by a compiler but also a high level language code that may be implemented by a computer using an interpreter, and the like.

The hardware devices may be configured to be operated by one or more software modules or vice versa to conduct the operation according to the embodiments.

Although the invention is described with reference to specific items such as specific elements, to merely some embodiments, and to drawings, such specific details disclosed herein are merely representative for purposes of helping more comprehensive understanding of the present invention. The present invention, however, is not limited to only the exemplary embodiments set forth herein, and those skilled in the art will appreciate that the present invention can be embodied in many alternate forms.

Therefore, the spirit of the present invention shall not be limited to the above-described embodiments, and the entire scope of the appended claims and their equivalents will fall within the scope and spirit of the invention.

The invention claimed is:

1. A device for measuring sleep efficiency by using a radar, the device comprising:

a height recognition unit recognizing a height of a measurement target person by using a signal received from the radar;

a movement section extraction unit extracting a movement section of the measurement target person during sleep from the received signal, and calculating a length of the extracted movement section and an amount of movement;

a normalization unit normalizing the amount of the movement by applying, to the calculated amount of the movement, a ratio between the height of the measurement target person and the length of the movement section;

a sleep/wakefulness state determination unit determining whether the measurement target person is in a wakefulness state or a sleep state by calculating a total amount of the movement per unit length for a predetermined time on the basis of the normalized amount of the movement and by comparing the calculated total amount of the movement with a predetermined threshold value; and a sleep efficiency calculation unit calculating the sleep efficiency by using a total sleep time, a time determined into the wakefulness state during the total sleep time, the number of times that the wakefulness state is determined, and a predetermined wakefulness state maintenance time in which the wakefulness state is expected to be maintained.

2. The device of claim 1, wherein the height recognition unit extracts a signal change section before and after the measurement target person lies on a place for measuring the sleep efficiency, and recognizes the height of the measurement target person by using the extracted signal change section.

3. The device of claim 1, wherein the height recognition unit adds up the extracted movement sections from the received signal and recognizes a distance between a start point and an end point of a sum of the movement sections as the height of the measurement target person.

4. The device of claim 1, wherein the height recognition unit converts a previously input height of the measurement target person by taking an actual installation position of the radar into consideration, and recognizes a value that results from the conversion as the height of the measurement target person.

5. The device of claim 1, wherein the movement section extraction unit extracts the movement section using a difference signal that is a difference between two signals consecutively received from the radar, and a case where the difference signal exceeds a predetermined threshold value is determined as the movement section, or the movement section is determined using constant false alarm rate(CFAR) for the difference signal.

6. The device of claim 1, wherein the sleep efficiency calculation unit calculates the sleep efficiency using Equation below, $$E = \frac{T_{total} - (T_M + \tau \cdot K)}{T_{total}} \times 100, \quad \text{[Equation]}$$

wherein E denotes the sleep efficiency, T total denotes the total sleep time, TM denotes the time determined into the wakefulness state, K denotes the number of times that the wakefulness state is determined, and $\tau$ denotes the predetermined wakefulness state maintenance time.

7. A method of measuring sleep efficiency by a sleep efficiency measurement device using a radar, the method comprising:

(a) recognizing a height of a measurement target person by using a signal received from the radar;

(b) extracting a movement section of the measurement target person during sleep from the received signal, and calculating a length of the extracted movement section and an amount of movement;

(c) normalizing the amount of the movement by applying, to the calculated amount of the movement, a ratio between the height of the measurement target person and the length of the movement section;

(d) determining whether the measurement target person is in a wakefulness state or a sleep state by calculating a total amount of the movement per unit length for a predetermined time on the basis of the normalized amount of the movement and by comparing the calculated total amount of the movement with a predetermined threshold value; and (e) calculating the sleep efficiency by using a total sleep time, a time determined into the wakefulness state during the total sleep time, the number of times that the wakefulness state is determined, and a predetermined wakefulness state maintenance time in which the wakefulness state is expected to be maintained.

8. The method of claim 7, wherein at the step (e), the sleep efficiency is calculated using Equation below, $$E = \frac{T_{total} - (T_M + \tau \cdot K)}{T_{total}} \times 100, \quad \text{[Equation]}$$

wherein E denotes the sleep efficiency, T total denotes the total sleep time, TM denotes the time determined into the wakefulness due to the movement, K denotes the number of times that the wakefulness is determined due to the movement, and $\tau$ denotes the predetermined wakefulness state maintenance time in which the wakefulness state is expected to be maintained.

\* \* \* \* \*